(12) United States Patent
Furia et al.

(10) Patent No.: US 8,118,747 B2
(45) Date of Patent: Feb. 21, 2012

(54) ERGONOMIC HOUSING FOR ELECTROACOUSTIC TRANSDUCERS PARTICULARLY FOR ULTRASOUND IMAGING AND ULTRASOUND PROBE WITH SAID HOUSING

(75) Inventors: Roberto Furia, Genoa (IT); Fabio Rezzonico, Como (IT)

(73) Assignee: Esaote, S.p.A., Milan (IT)

( * ) Notice: Subject to any disclaimer, the term of this patent is extended or adjusted under 35 U.S.C. 154(b) by 1009 days.

(21) Appl. No.: 12/001,933

(22) Filed: Dec. 13, 2007

(65) Prior Publication Data

US 2008/0146936 A1    Jun. 19, 2008

(30) Foreign Application Priority Data

Dec. 18, 2006    (EP) .................................... 06425843

(51) Int. Cl.
*A61B 8/14* (2006.01)
(52) U.S. Cl. ........................................................ 600/459
(58) Field of Classification Search .................. 600/437, 600/445, 447, 459, 463
See application file for complete search history.

(56) References Cited

U.S. PATENT DOCUMENTS

| 4,898,177 A | 2/1990 | Takano et al. ............ 128/662.03 |
| 5,752,517 A | 5/1998 | Harman et al. .......... 128/662.03 |
| 5,897,503 A | 4/1999 | Lyon et al. ................... 600/459 |
| 2003/0060714 A1 | 3/2003 | Henderson et al. ........... 600/459 |
| 2006/0173331 A1 | 8/2006 | Bonton et al. ................ 600/445 |

FOREIGN PATENT DOCUMENTS

| JP | 200334190 | 11/2003 |
| JP | 200339706 | 12/2003 |
| WO | WO 2005/053537 A2 | 6/2005 |

OTHER PUBLICATIONS

Search Report from European Patent Office from EP 06425843.7 (priority application) dated Sep. 27, 2007, 6 pgs.

*Primary Examiner* — Michael Rozanski
(74) *Attorney, Agent, or Firm* — Woodard Emhardt Moriarty McNett & Henry LLP

(57) ABSTRACT

An ergonomic housing for electroacoustic transducers, particularly for ultrasound imaging, includes at least an inner space (4) housing, one or more electroacoustic transducers (5) and possible further electric and/or electronic components (6/7). The housing (1) has at least an acoustic window (2) at which the one or more electroacoustic transducers (5) are placed. Further included is a handle part (101) composed of an opposing gripping surface having a shape that is ergonomically fitted for being gripped by a hand or a portion thereof. The gripping surface has such a shape or profile (301) to be ergonomically fitted for being gripped by inserting it in the hollow between two adjacent fingers of the hand.

26 Claims, 10 Drawing Sheets

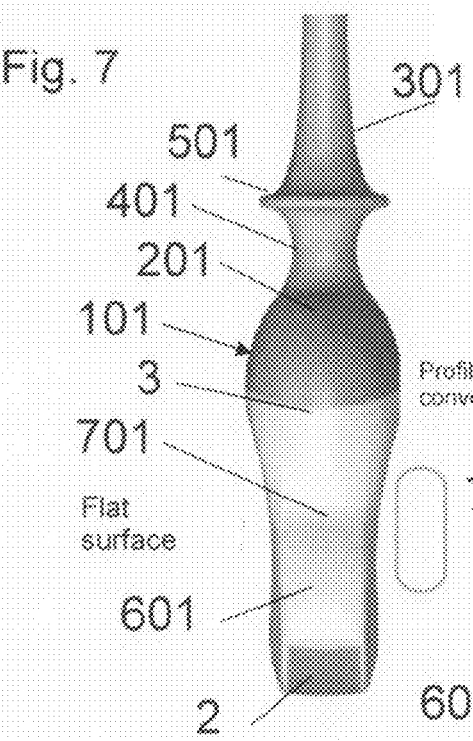
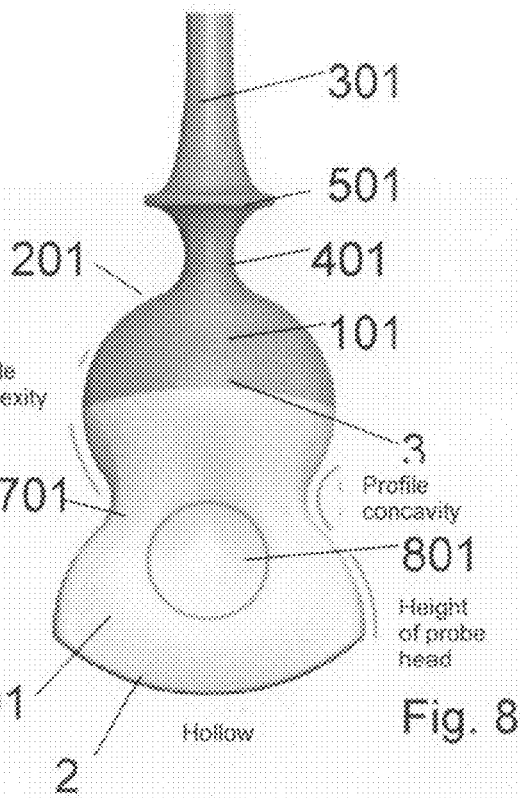
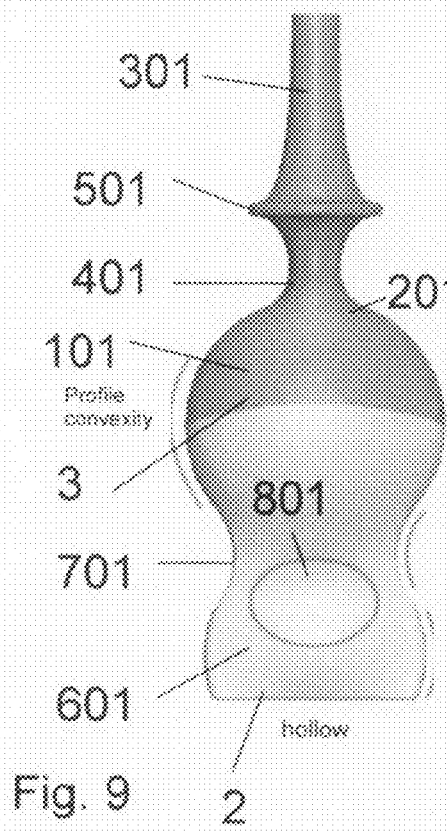
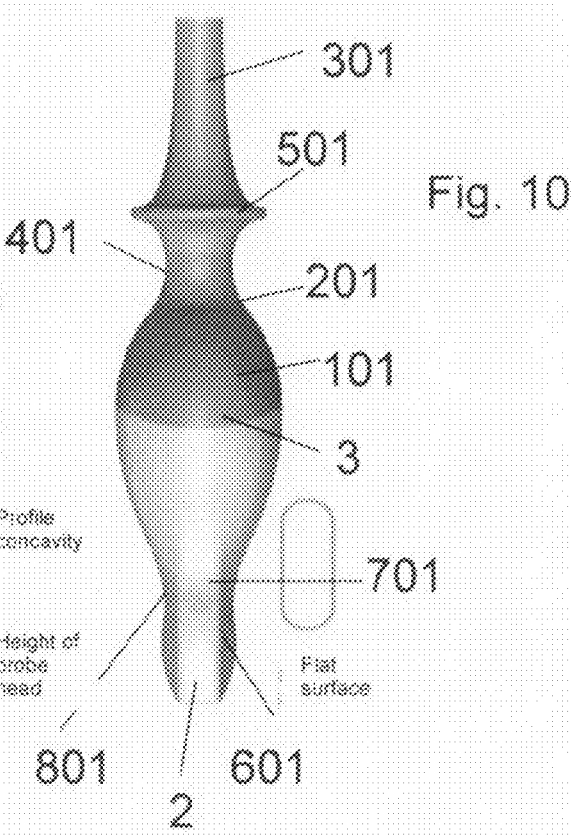

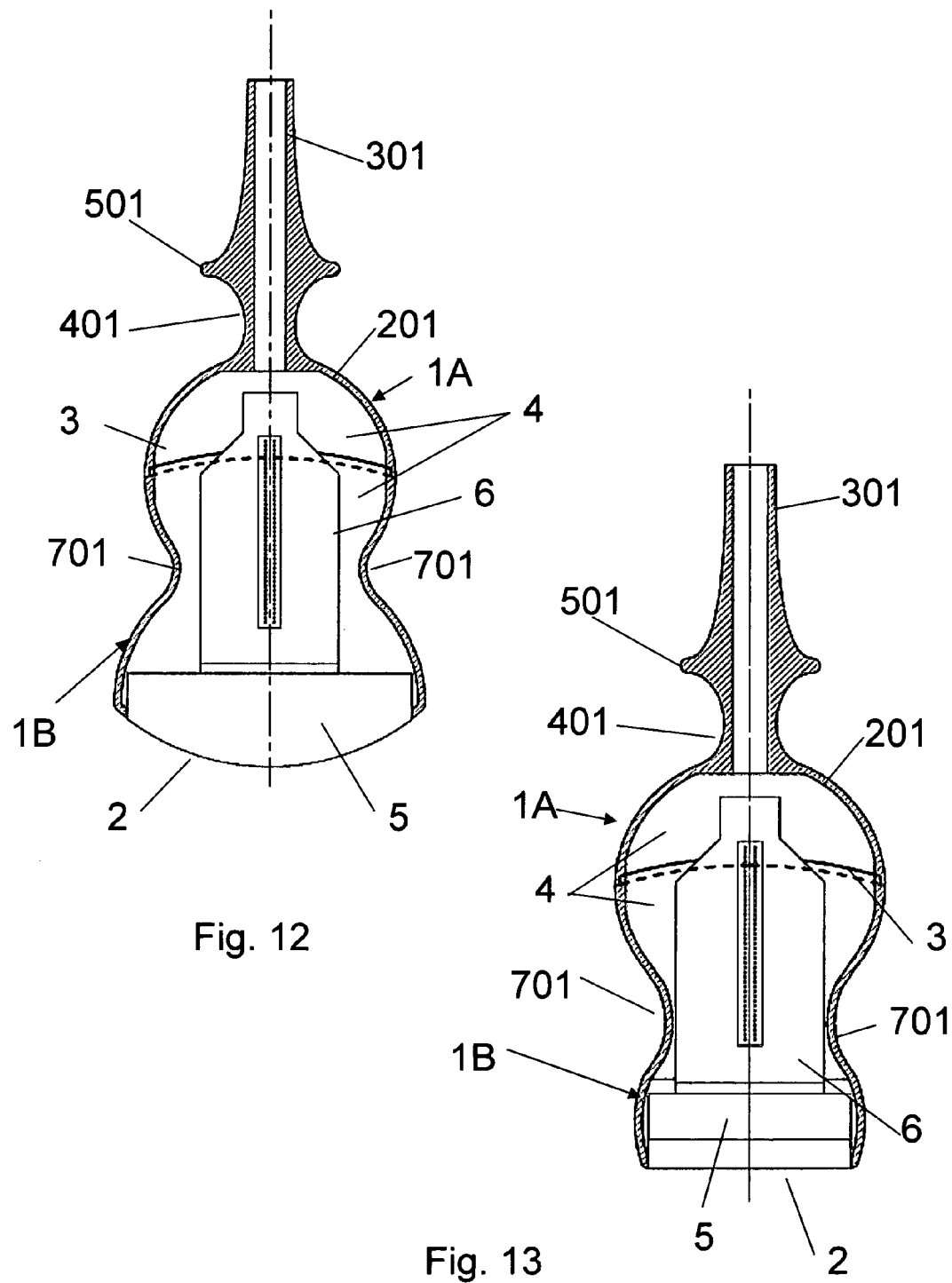

ERGONOMIC HOUSING FOR ELECTROACOUSTIC TRANSDUCERS PARTICULARLY FOR ULTRASOUND IMAGING AND ULTRASOUND PROBE WITH SAID HOUSING

CROSS REFERENCES TO RELATED APPLICATIONS

This application claims priority to European Patent Application No. EP 06425843.7, filed Dec. 18, 2006, entitled "ERGONOMIC HOUSING FOR ELECTROACOUSTIC TRANSDUCERS PARTICULARLY FOR ULTRASOUND IMAGING AND ULTRASOUND PROBE WITH SAID HOUSING", which is expressly incorporated by reference herein, in its entirety.

BACKGROUND OF THE INVENTION

The present invention relates to an ergonomic housing for electroacoustic transducers, particularly for ultrasound imaging, including at least an inner space housing, one or more electroacoustic transducers and possible further electric and/or electronic components. The housing has at least an acoustic window at which the one or more electroacoustic transducers are placed. Further included is a handle part composed of an opposing gripping surface having a shape that is ergonomically fitted for being gripped by a hand or a portion thereof.

Housings of this broad type or category are known in the technical field. The ultrasound imaging is considerably widespread and it is often used. By means of studies in the field it has been found that users of ultrasound systems have muscle-skeletal diseases of the hand, wrist, neck and back coinciding with the use of ultrasound probes.

In order to avoid or at least to reduce the above issues, housings whose shape has been ergonomically modified are known. One observation is that observed diseases can be eliminated or reduced by allowing the hand and the muscle-skeletal structure associated thereto to have relaxation moments. However, this must be done without losing the control of the probe such that when the examination is carried out the probe can be gripped with a sufficient security in order to guide it and to exert the necessary pressure against the patient.

One solution to this challenge is described in the document WO2005/053537 (Koninklijke Philips electronics N.V.) wherein in the location opposite to the acoustic window from which soundproofing pulses are emitted, the probe housing has a cap-like surface that is wide enough to allow the surface of the palm of the hand to grip the housing. The gripping surface, called a palmar gripping surface, is a kind of spherical or spheroidal gripping member that is gripped by the hand as a ball.

A similar solution is provided in the U.S. patent publication document US2006/0173331 (Siemens Corporation). In this disclosure, the housing of the probe provides a palmar gripping surface provided in an opposite location with respect to the acoustic window.

However, this palmar grip does not completely solve the above issues, since it does not allow the user to relax the hand without losing the grip on the housing of the probe. As such, the hand has to remain substantially tight on the surface of the housing forming the manual handle part. Even if during rest moments while the tightening force can somewhat be relaxed, the hand cannot be absolutely stretched in the correct relaxation position of the muscle-skeletal structure.

Even if such configuration of the housing for ultrasound probes providing the palmar grip increases somewhat the situation with respect to the conventional pen type grip by which the probe is held between the fingers (position called pinching in the technical jargon) for performing the scanning, probes providing a palmar grip do not allow to alternatively grip the probe by a pen type grip (pinching).

Considering the above, the present invention aims at providing an ergonomic housing for electroacoustic transducers, particularly for ultrasound imaging, for overcoming the issues with known housings and allowing one to surely hold the probe in the hand even in a position of substantial complete relaxation of the muscle-skeletal structure thereof.

The invention aims also at improving the housing such as to avoid drastic changes to the conventional structure of probes, to make simpler and to rationalize the manufacturing of ultrasound probes.

The invention achieves the above aims by providing an ergonomic housing for electroacoustic transducers, particularly for ultrasound imaging, of the type described herein. The housing has a shape or profile constructed and arranged to be ergonomically fitted for being gripped between two adjacent fingers of the hand, i.e. to be inserted in the hollow between two adjacent fingers of the hand of the user.

Advantageously the shape and sizes of the housing are such that the adjacent fingers of the hand holding the housing do not force fingers of the hand to be opened wide or to be tightened leading fingers to not be relaxed. On the contrary, particularly the shape and sizes of the housing are such to allow the holding between the two fingers in a natural relative spacing position thereof.

An advantageous embodiment provides the gripping surface of the housing to have a gripping surface that is ergonomically shaped in order to be gripped between the fingers, i.e. by interposing it in the hollow between two adjacent fingers of the hand.

The gripping extension to be held between the fingers is shaped such to be anatomically adapted to be engaged in the hollow between the fingers between two adjacent fingers of the hand, particularly between the forefinger and the middle finger or between the middle finger and the forefinger.

Advantageously the gripping surface of the housing from which the gripping extension to be held between the fingers comes out has a resting part that is like a spherical or spheroidal cap or dome and that is provided opposing the acoustic window, the gripping extension to be held between the fingers being provided at the top of the resting part.

The gripping extension that is held between the fingers may have various shapes and sizes. It can be also composed of an elongated member like a pen or the like having a rounded shape in section.

According to a further characteristic improving the security of the grip between the fingers, the gripping extension to be held between the fingers has at least a pair of opposite gripping recesses with a U-shaped section, each of which is intended for housing one of the two adjacent fingers for the engagement between the fingers of the gripping extension.

As a further improvement, the gripping extension that is held between the fingers has an annular recess having substantially a U-shaped section, whose bottom surface is formed by a band of shell axial surface connected in a rounded way with the two side surfaces that are formed by surfaces transverse to the longitudinal axis of the extension and connected to the bottom surface, possibly only one or both in a rounded way. One of the two side surfaces of the annular recess is composed of the resting part of the gripping surface and the other side surface is composed of the surface of a radial annular enlargement provided at a certain distance from the resting part of the gripping surface.

The gripping extension that is held between the fingers has a rotation symmetrical shape or alternatively a non-circular shape of the section, with a greater axis substantially oriented towards the fingers gripping it and/or in the antero-posterior direction of the hand and/or in the direction of the hollow between the fingers and with a smaller axis oriented in the direction transversal to the longitudinal axis of the fingers and/or to the antero-posterior direction of the hand.

In a related embodiment, the gripping extension that is held between the fingers is a sleeve for the introduction of an electrical cable for connecting the transducer.

Various relative arrangements of the acoustic window with respect to the gripping surface and with respect to the gripping extension that is held between the fingers are possible. A particular choice for example provides gripping extension that is held between the fingers to have a longitudinal axis that coincides with the prolongation of a vector perpendicular to the center of the acoustic window.

With regard to the acoustic window, it has to be shaped in a way corresponding to the array of electroacoustic transducers that can be linear, i.e. flat or curved such as in convex probes or the curvature may be according to two axes that are perpendicular one with respect to the other or anyway they are not parallel. In this case, the acoustic window is composed of a flat member or it has a curved configuration respectively only according to a curvature axis or according to two or more curvature axes there being possible also the fact that the curvature can be opposite to the one of the gripping surface.

In order to allow the gripping of the housing with a so called pen type grip (pinching), the housing has such a shape and such a thickness at least in a direction perpendicular to the longitudinal axis to be gripped with a position of the hand corresponding to the so called pen type grip, the shape and the thickness being provided for a part of the housing associated to the end having the acoustic window.

Other manufacturing variants improving the gripping comfort may provide the housing to have two opposite recesses with a section rounded shape, at an intermediate region of the housing, between the gripping surface and the acoustic window. Moreover the housing may have, from the intermediate region and in the direction of the acoustic window, two different thicknesses in the direction of each one of two axes perpendicular one with respect to the other and enclosed in the plane perpendicular to the axis of the gripping extension to be held between the fingers or in a plane tangential or parallel to the acoustic window.

The handle part of the housing forming the cap-like gripping surface opposite to the acoustic window, is advantageously composed of a spheroidal body that is flattened on two sides that are diametrically opposite one with respect to the other. This construction provides two different diameters, a greater one and a smaller one in the plane perpendicular to the axis of the gripping extension to be held between the fingers. The two opposite side recesses provided in the intermediate region of the housing are made as hollow ones in the direction of the greater axis.

Therefore the invention provides a housing made of a first housing part and a second housing part, which housing parts are harmonically completed one with the other and are divided along an intermediate separation plane between a part that is shaped so as to form a gripping handle with a pencil type grip position and a gripping handle part that is shaped such to be held by gripping it between fingers.

It is possible to provide the two housing parts to be integrally made or to be movably fastened one to the other or it is possible to provide the two housing parts to be movably fastened one to the other.

Still according to an advantageous characteristic of the present invention, the housing is provided in combination with one or more transducers, an electronic circuit, a cable connecting the electronic circuit to remote processing and control devices and a member connecting the cable to the electronic circuit. A part of the two cooperating connector parts is integral with the first housing part and the other one is integral with the second housing part. The two connector parts are automatically engaged and disengaged one with the other contemporaneously when the two housing parts are fastened and separated.

By the latter characteristic, it is possible to provide a first housing part that is firmly associated with transducers and with possible circuits and electric or electronic components, different combinations of first housing parts and transducers and possible circuits and electronic components that are different one with respect to the other being provided. While it is possible to provide only a second housing part that is firmly associated to the control cable, all first housing parts have a movable fastening end that is the same and it can be fastened and separated from only a second housing part.

Differently from present machines, by means of the above for different probes it is possible to provide the same cable that can be firmly integrated in the frame of an ultrasound machine for example, or possibly by providing also automatic winding means as in supplying and control cables of dental tools in so called dental drill units.

The present invention relates also to an ultrasound probe having a housing of the type described herein and a combination of ultrasound machine and probe with the housing described above. Further, the control and supplying cable of the ultrasound probe that is firmly integrated in the machine structure is mounted on automatic unwinding and winding means.

Further improvements of the housing, of the probe and of the ultrasound machine according to the present invention are described herein.

Characteristics of the invention and advantages deriving therefrom will be further understood from the following description and accompanying drawings.

BRIEF SUMMARY

An ergonomic housing for electroacoustic transducers, particularly for ultrasound imaging, includes an inner space housing, one or more electroacoustic transducers and possible further electric and/or electronic components. The housing has at least an acoustic window at which the one or more electroacoustic transducers are placed. Further included is a handle part composed of an opposing gripping surface having a shape that is ergonomically fitted for being gripped by a hand or a portion thereof.

One object of the present disclosure is to describe an improved ergonomic housing for electroacoustic transducers.

BRIEF DESCRIPTION OF THE SEVERAL VIEWS OF THE DRAWINGS

FIGS. 7 and 8 are two views similar to FIGS. 1 and 2 of a convex probe according to the present invention, wherein the probe housing can be separated in two parts thereof along a median plane.

FIGS. 9 and 10 are two views similar to FIGS. 1 and 2 of a linear probe according to the present invention, wherein the probe housing can be separated in two parts thereof along a median plane.

FIGS. 12 and 13 are a cross-section according to a median plane longitudinal and parallel to the wider face of a convex probe and a linear probe respectively, wherein the array of electroacoustic transducers and the possible electronics or electric circuitry are schematically indicated.

DETAILED DESCRIPTION

Figure 1:
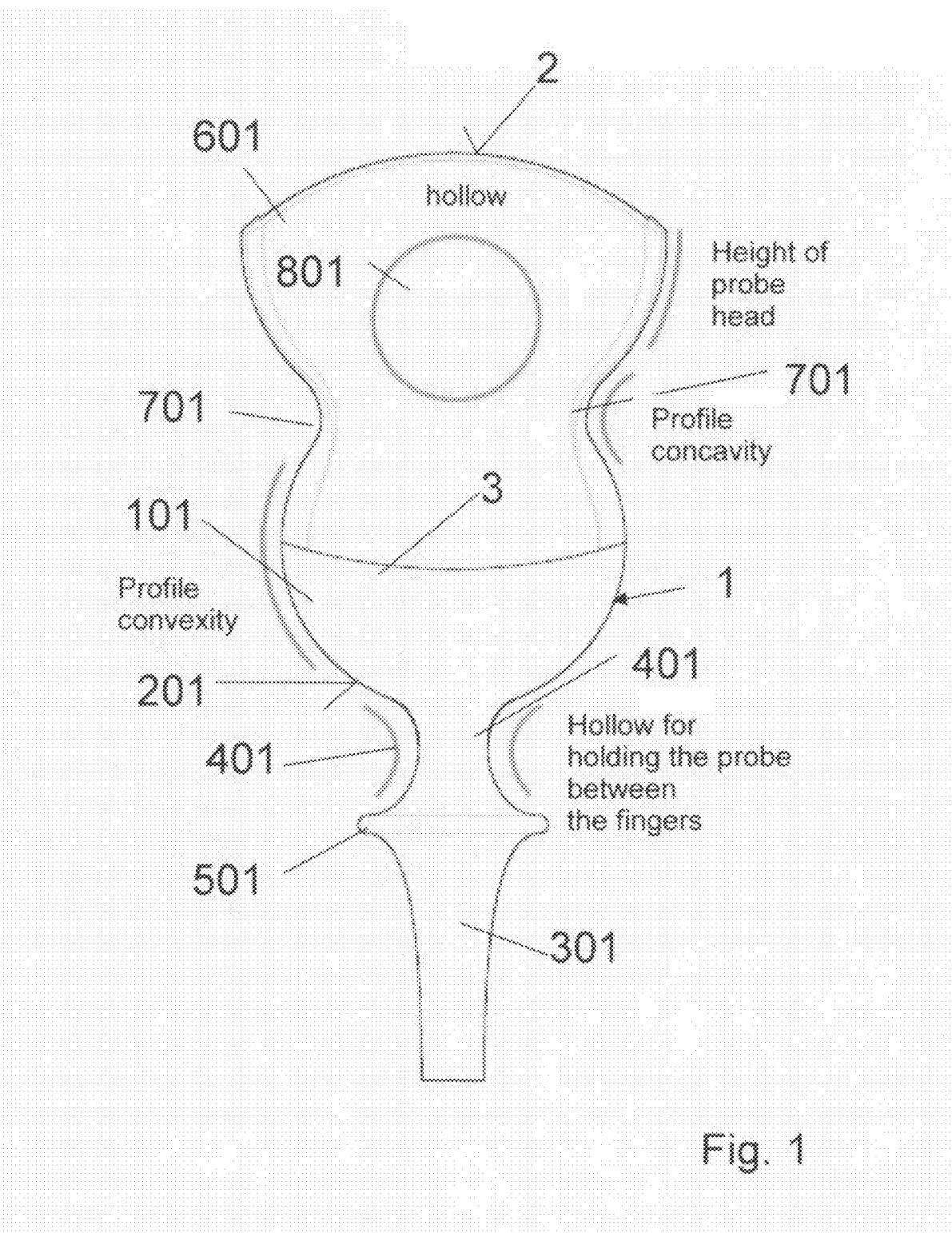
FIG. 1 is a side elevation view taken on the larger side of an ultrasound probe according to the present invention.

For the purposes of promoting an understanding of the disclosure, reference will now be made to the embodiments illustrated in the drawings and specific language will be used to describe the same. It will nevertheless be understood that no limitation of the scope of the disclosure is thereby intended, such alterations and further modifications in the illustrated device and its use, and such further applications of the principles of the disclosure as illustrated therein being contemplated as would normally occur to one skilled in the art to which the disclosure relates.

Figure 2:
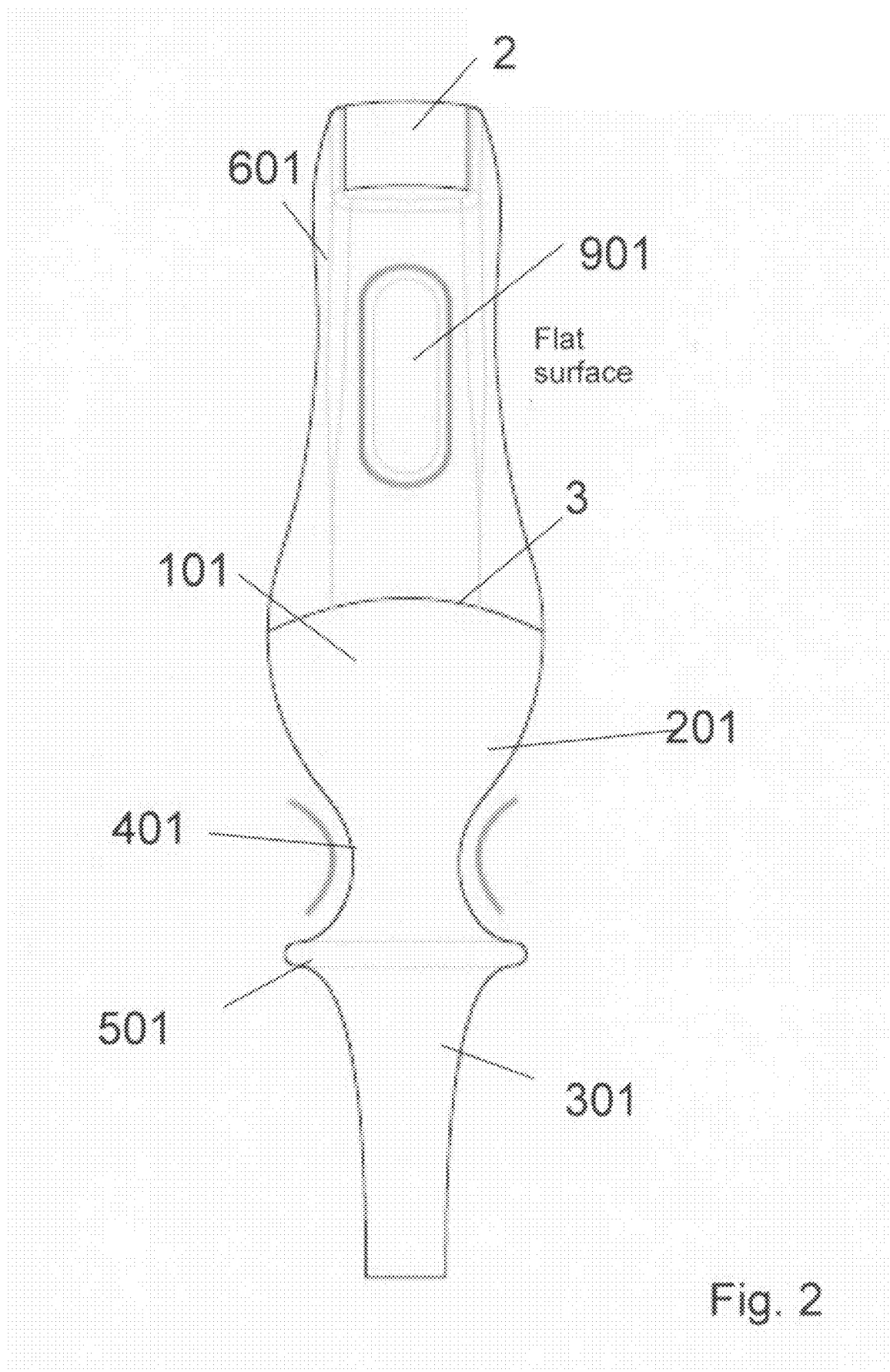
FIG. 2 is a side elevation view of the probe according to FIG. 1 but taken from the smaller side thereof.

In FIGS. 1 and 2 there is shown a probe of the type called convex, wherein electroacoustic transducers generating ultrasound pulses and receiving reflected ultrasound pulses being part of a transducer set, called an array, are arranged on a curved surface or are moved along a curved surface.

In this case the probe has a housing 1 that at one end, the one proximal to the object to be examined and particularly to the epithelial region coinciding with the anatomical region to be examined, has an acoustic window 2 behind which there is arranged the transducer array housed in a space enclosed by the housing 1.

The acoustic window 2 is composed of a wall portion that is permeable (i.e. transparent to ultrasound pulses), both the ones transmitted by transducers and the ones reflected towards the transducers.

The housing extends from the acoustic window in the direction of a distal end, (i.e. an end opposite to the one of the acoustic window). At such end the housing 1 forms a handle part 101 having a gripping and/or resting surface 201 that is rounded like a spherical or spheroidal cap or dome extending in the direction opposite to the end provided with the acoustic window 2 by a gripping extension to be held between the fingers denoted by 301. Such extension having a shape with a rounded cross section is connected to the gripping or resting surface 201 by at least two diametrically opposite recesses being shaped like a "U" denoted by 401 and which recesses 401 have a rounded bottom wall connected to a first side wall radially oriented with respect to the axis of the gripping extension 301 to be held between the fingers and composed of the region of the top of the gripping/resting surface 201. The opposite wall laterally delimiting the opposite U-shaped recesses 401 is composed of two diametrically opposite radial enlargements of the gripping extension 301 to be held between the fingers.

Advantageously such as shown in examples of figures instead of two opposite laid down U-shaped recesses it is advantageous to provide an annular groove of the gripping extension 301 to be held between the fingers delimited by two radial walls spaced in the direction of the axis of the extension and one of which is composed of the top portion of the gripping/resting surface 201, while the other one is composed of the radial annular surface of a radial enlargement 501 of the extension 401 that is provided as being spaced to a certain extent from the gripping/resting surface 201. The bottom of the annular groove is connected to the two annular, radial walls in a rounded and harmonic way.

Advantageously the distance between the two annular radial walls substantially corresponds to the average diameter or it is adapted to the average diameter of two adjacent fingers of a hand such that they can be partially housed in the groove or in the opposite recesses and such that the annular radial surface that is more far away from the acoustic window 2 partially overlaps the top of the hand and so of the corresponding two adjacent fingers between which the gripping extension to be held between the fingers is intended to be gripped.

The section of the extension is advantageously rounded and it can have different shapes.

In order to avoid the two adjacent fingers, generally but not exclusively the forefinger and the middle finger to take an unnatural and too much wide apart position at least at the region of the two opposite laid down U-shaped recesses 401 or of the annular groove, the section of the extension part corresponding to the region of the bottom of the groove is not rounded but it is flattened at the sides intended to be faced towards the two adjacent fingers. Therefore, in this case, the section is made oval or flattened such to have a smaller axis in the direction transverse to the fingers and to the hollow therebetween and a greater axis in the direction parallel to the longitudinal extension of the fingers and of the hollow therebetween. This allows to reduce the spreading of fingers such to have such a position guaranteeing a relaxed condition of the muscle-skeletal structure of the hand during the gripping condition between the fingers but also to guarantee a condition for the sufficient control or holding of the extension between the two fingers by means of an increased surface contacting the fingers in the longitudinal direction thereof.

The gripping/resting surface 201 is composed of an handle part like a spheric or spheroidal member or however a rounded member that is not a palmar gripping surface and having a maximum outwardly projecting equatorial line beyond which the handle part tapers connecting with a thinned handle part having a pen type grip denoted by 601 and ending by the end provided of the acoustic window 2.

The spheroidal handle part is connected to the tapered handle part 601 having the pen type grip with two hollow recesses 701 at diametrically opposite sides and that in the gripping condition between the fingers condition are a recess for gripping or housing the thumb of the hand. The two opposite recesses 701 are provided at the two side ends of the larger sides of the pen type grip tapered handle part 601, while the two narrower sides of the pen type grip tapered handle part are connected by a continuous flaring to the spheroidal handle part such as shown in FIG. 2.

In the median region of the two wider sides of the pen type grip tapered part 601 of the probe, the two wider sides have a hollow 801 for gripping or housing fingertips of the fingers in the pen type grip respectively.

Even if such characteristic is not to be considered a limitative one, but it is a simple advantageous configuration, in the shown embodiments the gripping extension 301 to be held between fingers is tubular and it is opened both at the end for the connection to the housing and to the opposite end and it is a sleeve for passing the cable for a cable for the control and communication of transducers and possible electronic and/or electric components associated to transducers with other units of an ultrasound machine. Such characteristic is seen in greater detail by sections according to diametral planes of FIGS. 12 and 13. However such double functionality of the gripping extension 301 to be held between fingers is only a particular case and it can be provided also in combination with a housing provided with different inlets for the control and communication cable (not shown in details in figures).

The above housing has such a shape that at a head end and particularly at the head end proximal to or contacting the epithelium of the patient is provided with an acoustic window 2 composed of a surface having a narrower side and a longer side. The surface may be flat or curved in a convex way. To the proximal head end there is connected a first pen type grip handle part denoted by 601 that is flattened having two wider sides parallel or substantially parallel to longer sides of the acoustic window and two narrower sides that are oriented in the direction of the narrower sides of the acoustic window 2.

The width of the two narrower sides, that is the distance between the two wider sides is such that the pencil type grip handle part 601 can be easily gripped between the fingers of the hand with the pen type grip and substantially it has a size corresponding to the thickness of a pen with a more or less large diameter.

In the central region of the two wider sides of the pen type grip handle part 601 there are provided two depressions or hollows 801 for easily tightening the part 601. These hollows allow closing of the opposite fingers like pliers when holding the probe like a pen, thus overcoming a circumference with an arc of 180° formed by pen type grip opposite fingers.

The pen type grip handle tapered part 601 is connected by two opposite side hollows made in the wider side walls to a handle spheroidal part 101 to be held between the fingers that is composed of a spheroidal member having a greater diameter in the direction parallel to wider sides of the pen type grip handle part 601 and a smaller diameter in the direction parallel to narrower sides of the pen type grip handle part 601. The spheroidal member on the side faced towards the end provided with the acoustic window 2 forms wall faces of recesses 701 in wider sides of the pen type grip handle part 601 and on the opposite side it forms a resting cap or dome that in its top region has the gripping extension 301 to be held between fingers with the annular groove 401 engaging the two adjacent gripping fingers delimited on one side by the cap or dome of the resting or gripping member 101 and on the other side by the radial enlargement 501.

In the particular embodiment the housing 1 has a longitudinal axis that coincides with a vector passing through the center of the acoustic window and perpendicular to the surface tangential to the acoustic window in the center such axis being coincident with the longitudinal axis of the gripping extension 401 to be held between the fingers and perpendicular to the greater and smaller diameter of the spheroid 101 in the equatorial plane thereof.

Figure 3:
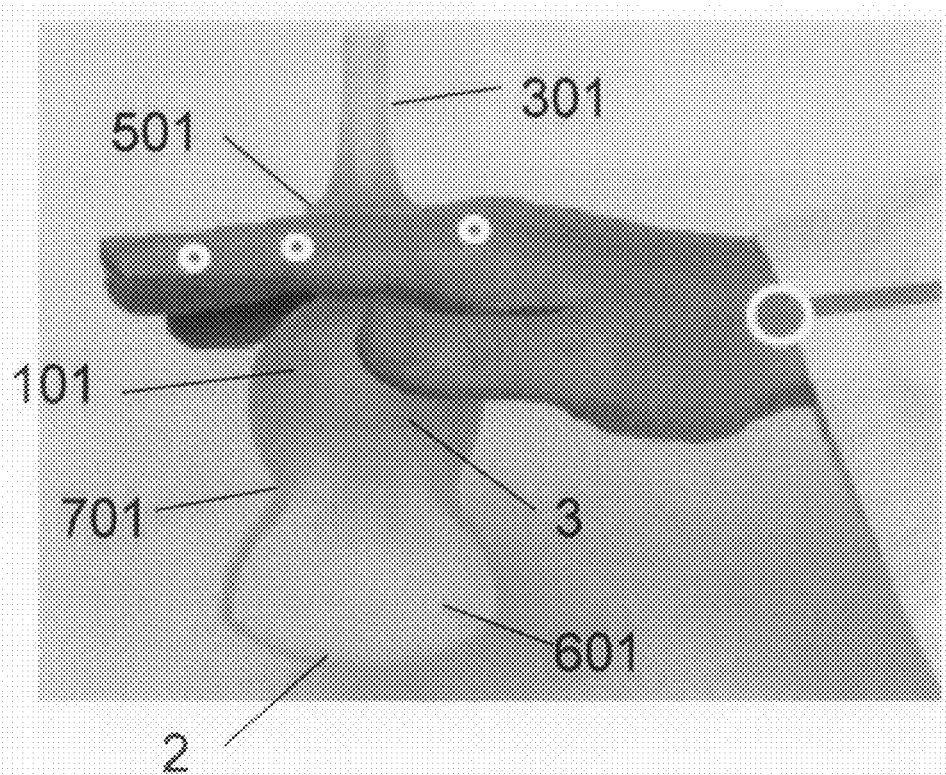
FIGS. 3 and 4 show conditions of the hand in positions holding the probe between the fingers under the relaxed condition of the hand and under the operating condition.
Figure 4:
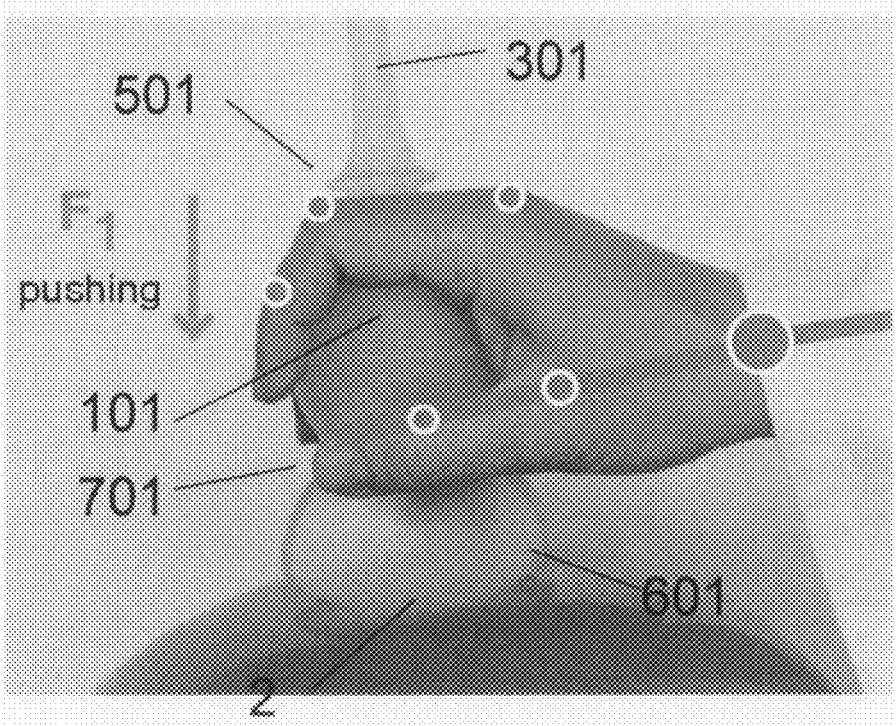

FIGS. 3 and 4 clearly show the advantage of gripping the housing between the fingers according to the present invention. In this example the skeletal structure of the hand is schematized by using an arrangement of articulated rods. Joints are indicated by circles. The greatest circle is the wrist. FIG. 3 clearly shows the fact that by means of the gripping extension to be held between the fingers it is possible to relatively firmly and securely grip the probe even if the hand is in its substantial resting and stretched position. In this case the probe is not subjected to any pressures and the grip is secure as regards the holding and the control of the probe when the hand and the probe are not stressed.

On the contrary FIG. 4 shows the holding between the fingers with the hand in its operating control condition wherein the probe is held not only by gripping it between the fingers, but also by tightening it or holding it like tongs along the resting and gripping cap or dome like surface 301. In this condition the thumb rests against the region of the handle spheroidal member under the equatorial line and connected to the pen type grip handle part 601. It is to be noted that the tongs-like or tightening grip occurs contemporaneously to the gripping between the fingers and however it is not a palmar grip. Moreover in this position tightening the holding between the fingers the spheroidal handle part 101 the joint of the wrist is not stressed i.e. the axis of the forearm and the one of the thumb are substantially aligned, thus reducing stresses to the carpal tunnel.

At the same time the possibility of resting the middle finger and/or other fingers of the hand on the cap or dome on the side of the spheroidal gripping part opposite to the acoustic window 2, on the distal side of the equatorial line of the spheroidal part allows to exert on the probe the necessary pushing pressure indicated by the arrow F1 in FIG. 4 and so to properly control the probe.

The following series of FIGS. 5A to 5E and 6A to 6E clearly show the modes for gripping the housing and so the probe according to the present invention with reference to a probe of the convex type and to a probe of the linear type.

Figure 5A:
FIGS. 5A to 5E are different positions for gripping a convex probe according to the present invention for alternatively the pen type grip and the grip between the fingers.
Figure 5B:
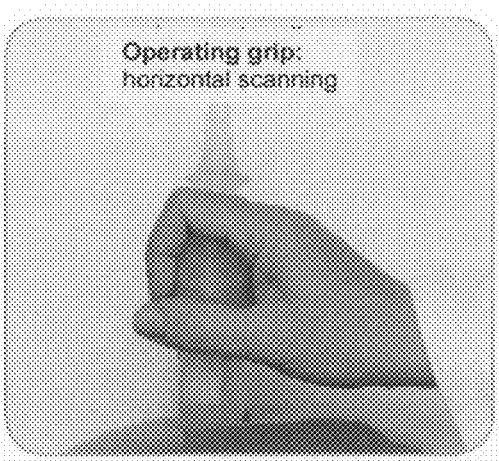
Figure 6A:
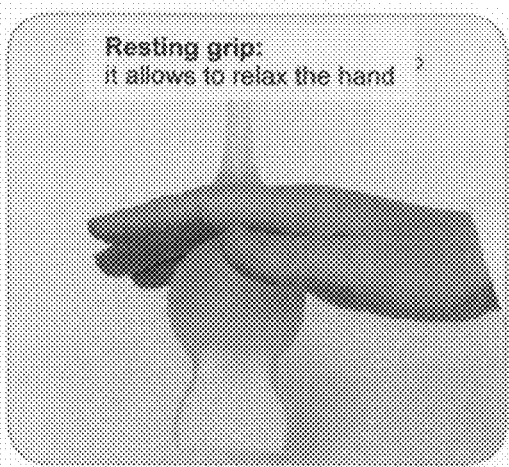
FIGS. 6A to 6E are different positions for gripping a linear probe according to the present invention for alternatively the pen type grip and the grip between the fingers.

FIGS. 5A and 6A show the gripping condition by the holding between the fingers with the hand in the stretched and resting condition. FIG. 5B and FIG. 6C show the condition when the housing is gripped between the fingers and the spheroid resting and gripping part 101 is tightened the wider faces of the housing and more precisely of the pen type grip handle part 601 or longer sides of the acoustic window 2 being oriented transversely to the longitudinal direction of fingers.

Figure 5C:
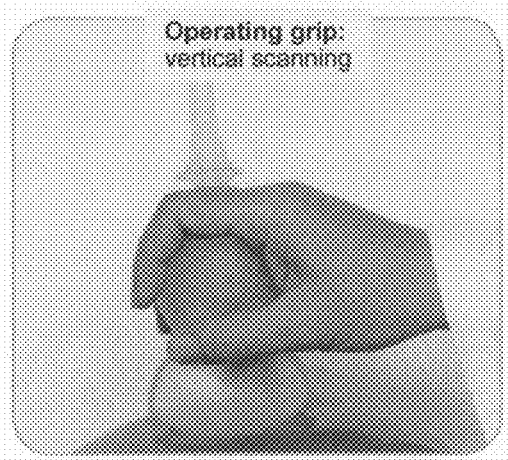
Figure 5D:
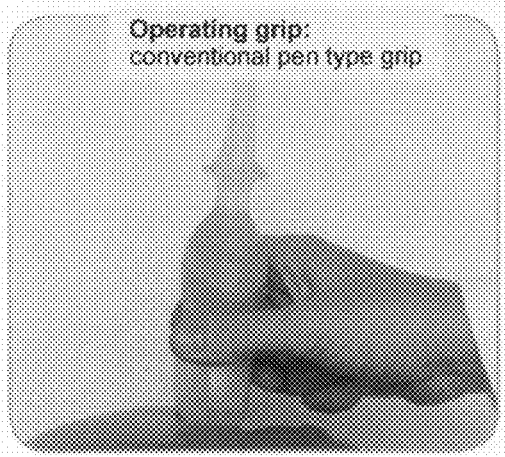
Figure 5E:
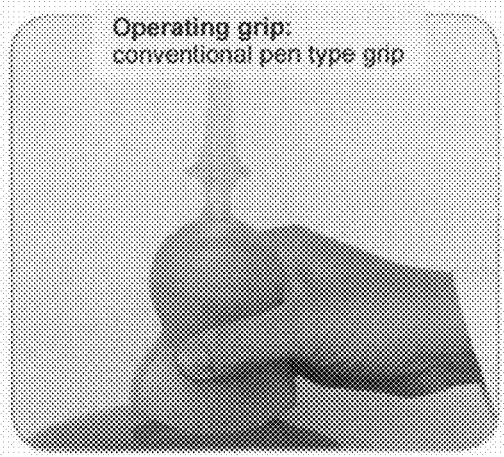
Figure 6B:
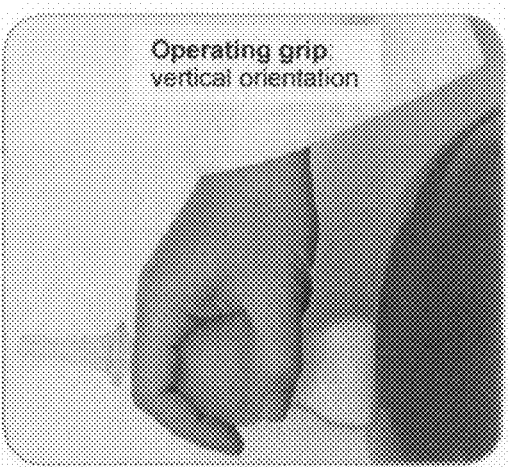
Figure 6C:
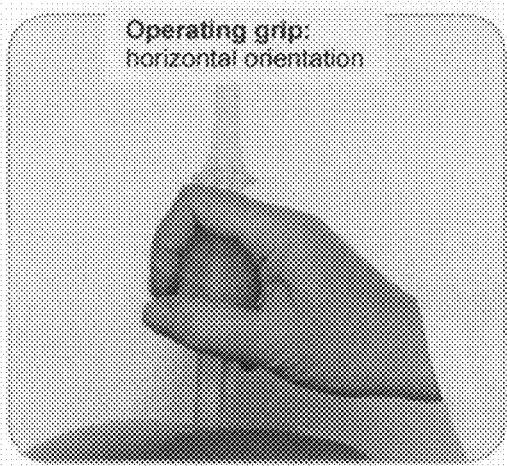
Figure 6D:
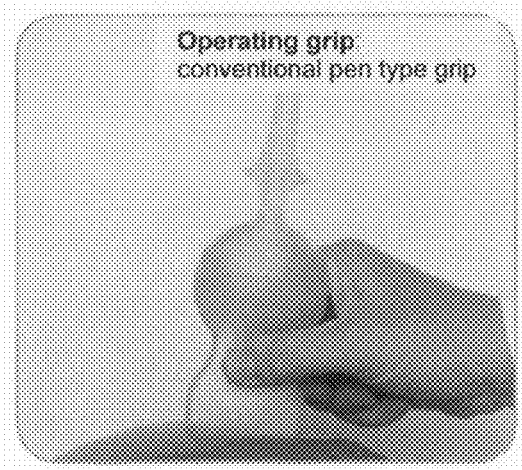
Figure 6E:
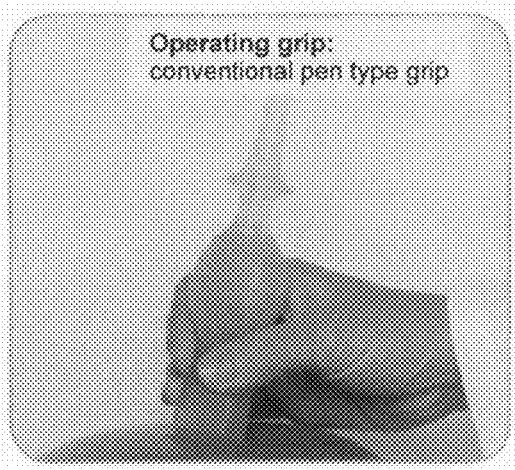
Figure 11:
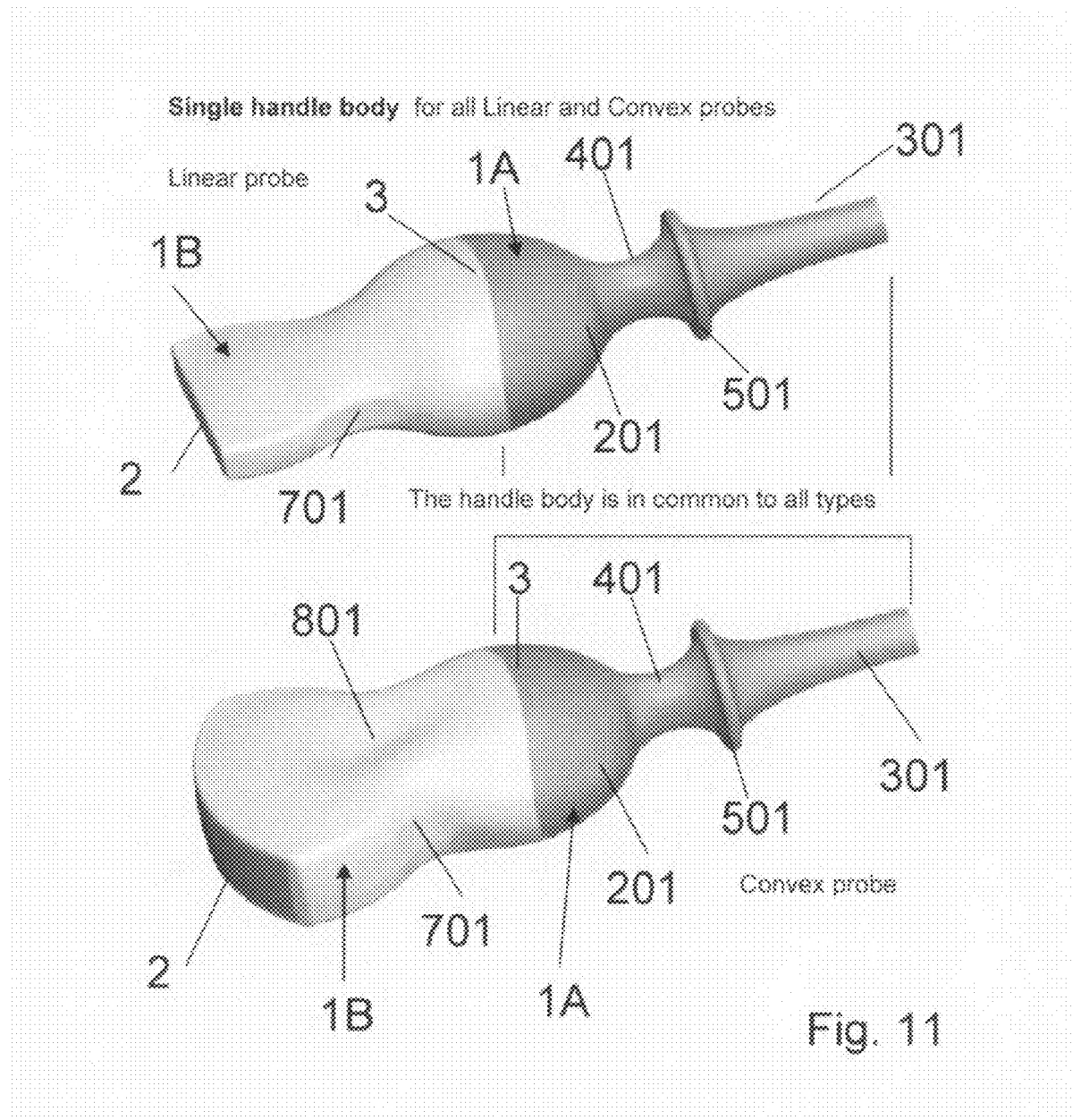
FIG. 11 is a variant embodiment of probes according to FIGS. 7 to 10, wherein the pen type gripping part and housing electroacoustic transducers and possible electronics of different configurations of probes can be movably fastened to a housing part composing the between-finger gripping part that is identical for all probes.

FIGS. 5C and 6B show the variant wherein the housing is gripped by tightening and holding between fingers the spheroid gripping and resting part 101 by using the wider faces of the housing and more precisely of the pen type grip handle part 601 or with the longer sides of the acoustic window 2 substantially oriented in the longitudinal direction of fingers.

FIGS. 5D and 5E and FIGS. 6E and 6D show the housing gripped by the pen type grip with the probe in the two positions respectively with respect to the longitudinal axis of the hand respectively and that is in the two positions of the probe or housing corresponding to an orientation of the wider sides of the housing or of the flattened part 601 of the probe transverse to the axis of the forearm or parallel thereto respectively.

FIGS. 7 to 15 show probes of the convex type and of the linear type according to what has been previously described.

As it is clear from FIGS. 7 to 15, the two housing parts 101 and 601 composing the spheroidal handle gripping or resting part and the pen type grip handle part respectively, are advantageously made as being movably fastenable along a substantially equatorial separation plane of the spheroidal part 101. Such plane coincides with the line separating the walls of the two housing parts 101 and 601 denoted by 3 in FIGS. 7 to 15.

The two housing parts 101 and 601 can be made of different materials and particularly the spheroidal gripping one can be made of a soft material and the pen type grip handle one can be made of a more rigid material.

The softer material can be also an outer layer covering a more rigid supporting layer. Similarly it is also possible for one part 101 or the other one 601 to have regions with covering inserts or layers made of soft material in locations contacting the fingers or other parts of the hand, such as for example hollows 801 or islets 901 in recesses 401.

Advantageously this characteristic allows to make housings for ultrasound probes and ultrasound probes such that the cap-like or dome-like part bearing the gripping extension 301 to be held between the fingers is in common to a series of probes which have as the probe housing the pen type grip handle part 601 and the spheroidal gripping part extending to the substantially equatorial separation surface.

In this case, such as shown in FIGS. 12 to 15, in the housing space 4 of the housing there is the enclosed the array of electroacoustic transducers 5 placed at the acoustic window 2, a terminal board composed of a printed circuit 6 or it can be composed of simple conducting paths or it can also comprise an electronic circuit with corresponding electronic components and a connector 7 mounted on the printed circuit and connecting a control and communication cable (not shown) to the printed circuit and to transducers.

In FIGS. 11 to 15 the two housing parts are defined by reference numbers 1A and 1B since the fact of being different is not related to the gripping task but it is related to the two parts that can be coupled or uncoupled and from a functionality point of view they coincide only partially with definitions of spheroidal gripping and resting part 101 and pen type grip handle part 601. Particularly as it results from FIGS. 14 and 15, the connector 7 is made of two parts 107 and 207 that can be coupled and uncoupled both mechanically and electrically, the two parts being firmly mounted one 107 to the printed circuit 6 in the housing part 1B and the other one 207 in the housing part 1A wherein it is firmly connected to the control and communication cable (not shown) passing inside the housing part 1A through the gripping extension 301 to be held between the fingers.

The two connector parts are made and mounted such that the mechanical and electric coupling of the two connector parts 107, 207 occurs by the same or a part of the same relative movement coupling or uncoupling the two housing parts 1A and 1B, so that contemporaneously to the fastening of the two housing parts 1A and 1B and contemporaneously to the separation of the two housing parts 1A and 1B also the mechanical and electric coupling and the mechanical and electric uncoupling of the two connector parts 107 and 207 occur respectively.

Figure 14:
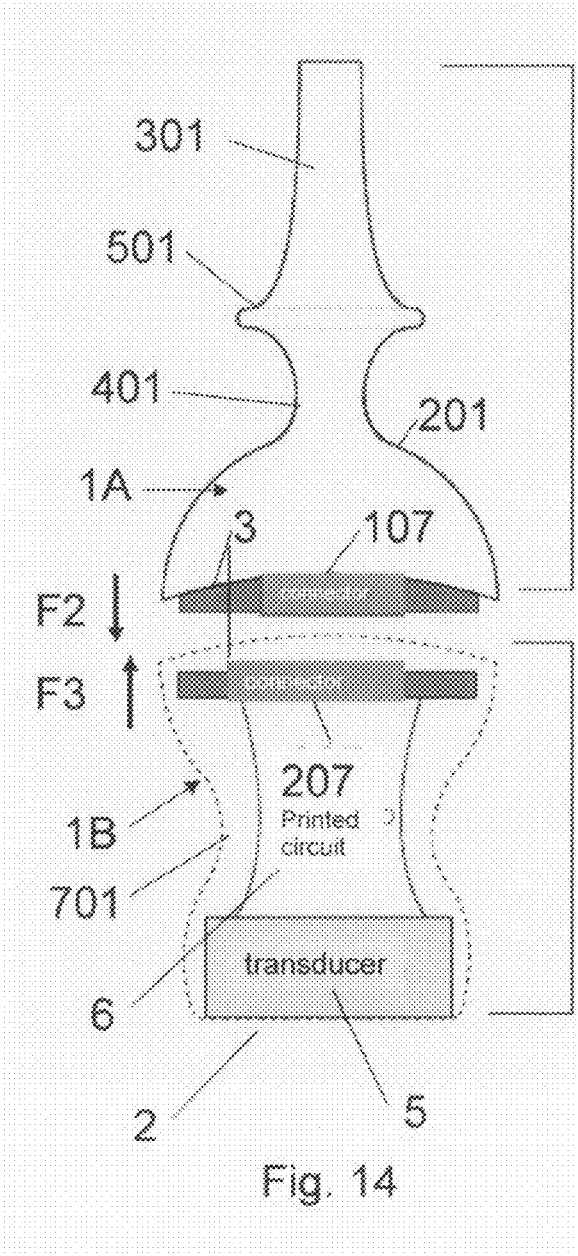
FIGS. 14 and 15 schematically show a linear probe according to the present invention and according to previous FIGS. 11 to 13.
Figure 15:
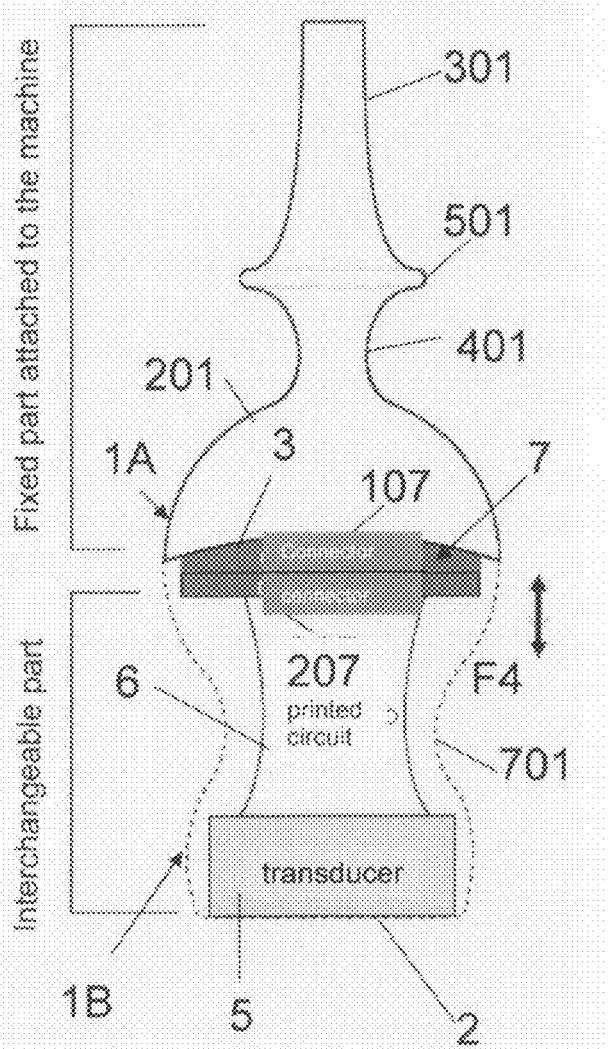

In the schematic example of FIGS. 14 and 15, the two housing parts 1A and 1B and the corresponding two connector parts 107 and 207 are coupled by approaching and compressing them in the direction of arrows F2 and F3 of FIG. 14 and they are uncoupled by pulling and bringing them farther away according to the double arrow F4 in FIG. 15. The arrows are oriented parallel to the longitudinal axis coinciding with the central axis of the acoustic window 2 that is perpendicular to the plane tangential to the center of the acoustic window and that possibly it also coincides with the axis of the gripping extension 301 to be held between the fingers.

It is to be noted that in the case of the example of FIGS. 11 to 15, the probe housing is composed of a part 1A that is always the same and it is both the terminal connecting the control and communication cable of the ultrasound machine to the ultrasound probe intended as the array of transducers and circuits associated thereto inside the probe, and a part of the spheroidal resting and gripping part 101 and more precisely the dome or cap-like part provided at the distal end of the probe housing and opposite to the acoustic window 2 and moreover it comprises the gripping extension 301 to be held between the fingers.

The other housing part 1B on the contrary becomes the real housing part of the probe firmly housing transducers and circuits associated thereto and it is different for each different probe, moreover the housing part 1B being composed of the pen type grip handle part 601 and of the part of the spheroidal gripping and resting part 101 connected to the pen type grip handle part and that is interposed between it and the substantially equatorial plane or line of separation 3, while all different probes have a housing composed of the housing part 1B and all the housing parts 1B have the same configuration and the identical coupling means, as well as an identical connector part 107 by means of which each of them can be coupled to the housing part 1A and to the corresponding connector part 207.

Figure 16:
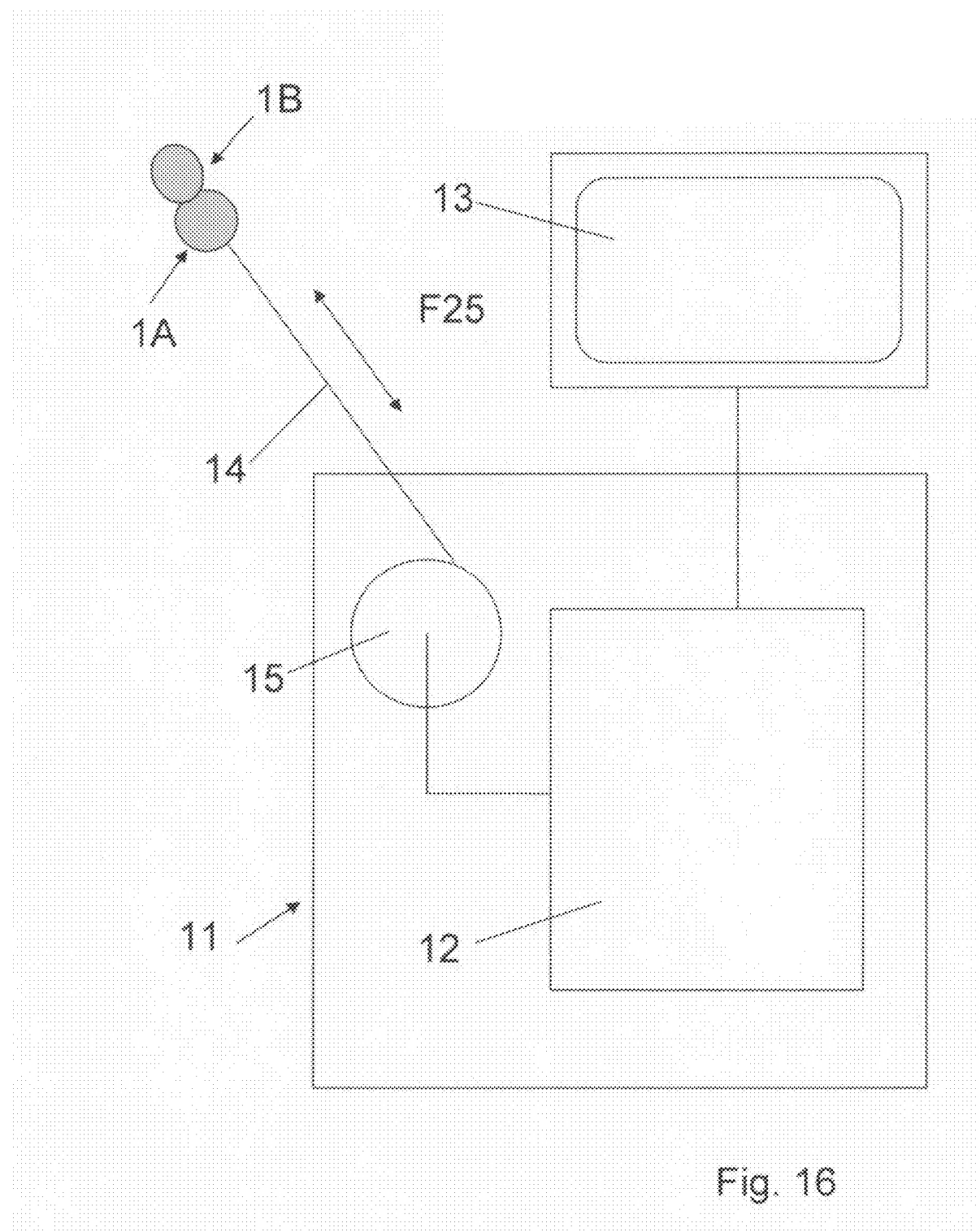
FIG. 16 schematically shows an ultrasound machine wherein the cable communicating and controlling the probe is firmly mounted in the machine by an automatic winding arrangement.

This embodiment allows to achieve a considerable advantage as it is shown in FIG. 16. In this figure by the number 11 a general machine for acquiring ultrasound images is indicated. The machine comprises circuits 12 controlling the ultrasound probe 1 and processing signals kept by the probe as images that are displayed on a screen 13 or by other alternative displaying means. The probe 1 is connected to control and processing circuits 12 by a control and processing cable 14. This cable is made as firmly connected or coupled to the ultrasound machine and particularly to control and processing circuits 12, while it ends with a housing part 1A with a connector part 207 to which a probe can be connected and whose housing is composed of a housing part 1B with a connector 107 according to what has been described with reference to FIGS. 11 to 15. In this case, therefore for changing the type of probe it is not necessary to replace the control and communication cable 14, but only the probe. Moreover this arrangement in combination with the cable 14 allows to provide automatic means 15 for winding the cable 14 on a reel for example composed of a reel upon which a certain length of the cable is wound and that is rotatable in the unwinding direction against the action of spring means operating the rotation of the reel in the winding direction. The means, for example a spiral spring, are loaded by the rotation of the reel when unwinding the cable occurring by means of the pulling action exerted by the user, so when the pulling force is released, the reel is rotationally dragged in the opposite direction i.e. in the winding direction and the cable is automatically rewound.

The functionality can be achieved also by means of other means for example with similar alternative means or by means substantially identical to means associated to cables or ducts controlling and supplying dental tools in so-called dental drill units.

From the above advantages of the present invention are clear consisting in a better condition for using the probe as regards the gripping thereof and consequences of an extended use on the health conditions of the muscle-skeletal structure of the hand and/or of the wrist of the user and at the same time in modifying the present manufacturing of probes by providing a combination of a series of probes that can be coupled to a sole connector connecting a control and communication cable that is firmly associated to the ultrasound machine and therefore it can be provided in combination with automatic lengthening and shortening mechanisms. In this case costs are reduced since all probes are connected to the same cable, and moreover the security and comfort in using the device drastically increases.

While the preferred embodiment of the invention has been illustrated and described in the drawings and foregoing description, the same is to be considered as illustrative and not restrictive in character, it being understood that all changes and modifications that come within the spirit of the invention are desired to be protected.

The invention claimed is:

1. An ergonomic housing for electroacoustic transducers for ultrasound imaging, comprising:
    at least one inner space housing;
    at least one electroacoustic transducer;
    at least one other electrical component;
    at least one acoustic window at which the at least one electroacoustic transducer is placed;
    a spheroidal handle part composed of an opposing gripping surface having a shape that is ergonomically fitted for being gripped by a hand or a part thereof, said gripping surface providing a gripping extension that is shaped to be anatomically fitted for the engagement in the space between two adjacent fingers of the hand; and
    an intermediate handle part defining two hollow recesses positioned on diametrically opposite sides, the intermediate handle part located between the gripping surface and the at least one acoustic window, the intermediate handle part constructed and arranged to be gripped between a thumb and finger of the hand,
    wherein the gripping extension includes a radial annular enlargement and a portion adjacent to the spheroidal handle part, said radial annular enlargement having a first diameter, said portion having a second diameter smaller than the first diameter.

2. The ergonomic housing according to claim 1, characterized in that the gripping surface has a resting part having a spherical shape, the resting part is positioned opposite to the at least one acoustic window, the gripping extension is positioned at the top of said resting part.

3. The ergonomic housing according to claim 2, characterized in that the gripping extension has at least one pair of opposite gripping recesses with a laid down U-shaped section, each of said at least one pair of opposite gripping recesses are constructed and arranged to house one of the two adjacent fingers for the engagement between the fingers and said gripping extension.

4. The ergonomic housing according to claim 3, characterized in that the at least one pair of opposite gripping recesses has a bottom wall that is oriented in an axial direction of the gripping extension, a first side wall and a second side wall both perpendicular to the axial direction of the gripping surface, the first side wall being composed of a region of a resting part and the second side wall being provided at a distance adapted to the size of human fingers.

5. The ergonomic housing according to claim 4, characterized in that the gripping extension has an annular recess having a laid down U-shaped section, said U-shaped section has a bottom surface formed by a band of shell axial surfaces connected in a rounded way with the first side wall and the second side wall surfaces that are formed by surfaces transversal to the longitudinal axis of the extension and connected to said bottom surface, while one of said two side surfaces of the annular recess is composed of the resting part of the gripping surface and the other side surface is composed of the surface of the radial annular enlargement provided at a certain distance from the resting part.

6. The ergonomic housing according to claim 2, characterized in that the at least one acoustic window has a curved arrangement according to at least one axis of curvature, the curved arrangement being positioned opposite the resting part of the gripping surface.

7. The ergonomic housing according to claim 1, characterized in that the gripping extension is composed of an elongated member having a rounded shape.

8. The ergonomic housing according to claim 1, characterized in that the gripping extension has a rotation symmetrical shape.

9. The ergonomic housing according to claim 1, characterized in that the gripping extension has an elliptical cross-section with a major axis substantially oriented in the antero-posterior direction of the hand and with a minor axis oriented in the direction transversal to the antero-posterior direction of the hand.

10. The ergonomic housing according to claim 1, characterized in that the gripping extension defines a sleeve for the introduction of an electrical cable for connecting the at least one electroacoustic transducer.

11. The ergonomic housing according to claim 1, characterized in that the gripping extension has a longitudinal axis that coincides with the prolongation of a vector perpendicular to a surface tangential to the center of the at least one acoustic window.

12. The ergonomic housing according to claim 1, characterized in that the at least one acoustic window is composed of a flat member.

13. The ergonomic housing according to claim 1, characterized in that the gripping surface is composed of a spheroidal body flattened on two diametrically opposite sides such to have two different diameters in the equatorial plane and one of which is a greater diameter and the other one is a smaller diameter in the plane, the two opposite side recesses provided at the intermediate handle part being made hollow in the direction of a major axis.

14. The ergonomic housing according to claim 13, characterized in that the spheroidal body is configured to be gripped by being tightened by fingers of the hand in addition to holding between the fingers the gripping extension.

15. The ergonomic housing according to claim 1, characterized in that the ergonomic housing has two different thicknesses in the direction perpendicular to the axial direction of the gripping extension.

16. The ergonomic housing according to claim 1, characterized in that the ergonomic housing is shaped to provide a pen type grip.

17. The ergonomic housing according to claim 1, characterized in that in the ergonomic housing has a flattened portion between the gripping surface and the at least one acoustic window shaped to form a pen type grip handle.

18. The ergonomic housing according to claim 17, characterized in that in the pen type grip handle has two opposite faces, the opposite faces having opposite depressions.

19. The ergonomic housing according to claim 17, characterized in that the ergonomic housing comprises the at least one acoustic window provided on the head side of the flattened portion which extends in the direction opposite to the at least one acoustic window with a spheroidal body provided at the top opposite to the acoustic window of the gripping extension.

20. The ergonomic housing according to claim 19, characterized in that the ergonomic housing is made of a first housing part and a second housing part, said first housing part and said second housing parts are harmonically connected and are separated along an intermediate separation plane between the pen type grip handle and the gripping surface.

21. The ergonomic housing according to claim 20, characterized in that the first housing part and the second housing part can be movably fastened one with the other.

22. The ergonomic housing according to claim 21, characterized in that the ergonomic housing is provided in combination with at least one electroacoustic transducers, an electrical circuit, a cable connecting the electrical circuit to a remote processing unit, a connecting member connecting the cable to the electrical circuit, the connecting member having a first connector part and a second connector part that can be mechanically and electrically coupled and uncoupled, the first connector part being provided integral with the first housing part and the second connector part being provided integral with the second housing part, the first connector part and second connector part being automatically engaged and disengaged one with the other contemporaneously when said first housing part and second housing part are fastened and separated.

23. The ergonomic housing according to claim 1, characterized in that the outer surface of the handle part is made of a soft material.

24. An ultrasound probe comprising at least one electroacoustic transducer connected to a communication cable, said at least one electroacoustic transducer being housed in a space of a housing of said probe, said housing comprising an acoustic window at which the at least one electroacoustic transducer is provided and a spheroidal handle part located opposite to the acoustic window, said spheroidal handle part composed of an opposing gripping surface comprising a gripping extension ergonomically shaped to be held between human fingers, said housing further comprising an intermediate handle part defining two hollow recesses positioned on diametrically opposite sides, the intermediate handle part located between the gripping surface and the acoustic window, the intermediate handle part constructed and arranged to be gripped between a thumb and finger of a human hand, wherein the gripping extension includes a radial annular enlargement and a portion adjacent to the spheroidal handle part, said radial annular enlargement having a first diameter, said portion having a second diameter smaller than the first diameter.

25. An ultrasound machine comprising means for controlling an ultrasound probe and means for processing receiving signals of the ultrasound probe and an ultrasound probe connected to said controlling and processing means by a control and communication cable, characterized in that the control and communications cable is firmly associated to the ultrasound machine there being provided with a terminal for the connection to the probe comprising at least one electroacoustic transducer connected to the control and communications cable, said at least one electroacoustic transducer being housed in a space of a housing of said probe, said housing comprises an acoustic window at which the at least one electroacoustic transducer is provided and a spheroidal handle part located opposite to the acoustic window, said spheroidal handle part composed of an opposing gripping surface comprising a gripping extension ergonomically shaped to be held between human fingers, said housing further comprising an intermediate handle part defining two hollow recesses positioned on diametrically opposite sides, the intermediate handle part located between the gripping surface and the acoustic window, the intermediate handle part constructed and arranged to be gripped between a thumb and finger of the human hand, wherein the gripping extension includes a radial annular enlargement and a portion adjacent to the spheroidal handle part, said radial annular enlargement having a first diameter, said portion having a second diameter smaller than the first diameter.

26. The ultrasound machine according to claim 25, characterized in that the control and communication cable is provided in communication with means for winding and unwinding a reel.

* * * * *